(12) United States Patent
Zhang (10) Patent No.: US 9,549,681 B2
(45) Date of Patent: Jan. 24, 2017

(54) MATRIX-BASED PATIENT SIGNAL ANALYSIS

(71) Applicant: Siemens Medical Solutions USA, Inc., Malvern, PA (US)

(72) Inventor: Hongxuan Zhang, Palatine, IL (US)

(73) Assignee: SIEMENS MEDICAL SOLUTIONS USA, INC., Malvern, PA (US)

( * ) Notice: Subject to any disclaimer, the term of this patent is extended or adjusted under 35 U.S.C. 154(b) by 95 days.

(21) Appl. No.: 14/546,538

(22) Filed: Nov. 18, 2014

(65) Prior Publication Data

US 2016/0135704 A1    May 19, 2016

(51) Int. Cl.
| | |
|---|---|
| A61B 5/04 | (2006.01) |
| A61B 5/0432 | (2006.01) |
| A61B 5/0456 | (2006.01) |
| A61B 5/0472 | (2006.01) |
| A61B 5/044 | (2006.01) |
| A61B 5/00 | (2006.01) |

(52) U.S. Cl.
CPC ......... *A61B 5/04012* (2013.01); *A61B 5/0006* (2013.01); *A61B 5/044* (2013.01); *A61B 5/0432* (2013.01); *A61B 5/0456* (2013.01); *A61B 5/0472* (2013.01)

(58) Field of Classification Search
CPC . A61B 5/04012; A61B 5/0452; A61B 5/0456; A61B 5/0472
See application file for complete search history.

(56) References Cited

U.S. PATENT DOCUMENTS

| | | |
|---|---|---|
| 4,457,312 A | 7/1984 | Ornato et al. |
| 5,054,496 A | 10/1991 | Wen et al. |
| 6,368,284 B1 | 4/2002 | Bardy |
| 7,123,963 B2 | 10/2006 | Sawchuk et al. |
| 7,231,244 B2 | 6/2007 | Laitio et al. |
| 7,430,309 B2 | 9/2008 | Harel et al. |
| 7,620,449 B2 | 11/2009 | Shvilkin et al. |
| 7,627,367 B2 | 12/2009 | Warren et al. |
| 7,761,141 B2 | 7/2010 | Hirsh |
| 7,769,437 B2 | 8/2010 | Zhu et al. |
| 7,783,340 B2 | 8/2010 | Sanghera et al. |
| 7,813,792 B2 | 10/2010 | Xue et al. |
| 7,894,889 B2 | 2/2011 | Zhang |
| 7,904,153 B2 | 3/2011 | Greenhut et al. |
| 7,925,348 B1 | 4/2011 | Bornzin et al. |
| 7,996,070 B2 | 8/2011 | Van Dam et al. |
| 8,010,347 B2 | 8/2011 | Ricci et al. |
| 8,024,030 B2 | 9/2011 | Douglas et al. |
| 8,108,037 B1 | 1/2012 | Krishnaswamy et al. |
| 8,160,684 B2 | 4/2012 | Ghanem et al. |
| 8,380,293 B2 | 2/2013 | Zhang et al. |
| 8,412,503 B2 | 4/2013 | Yamamoto |
| 8,473,050 B2 | 6/2013 | Kwok et al. |

*Primary Examiner* — Tammie K Heller (57) ABSTRACT

Disclosed herein is a framework for facilitating patient signal analysis. In accordance with one aspect, the framework generates a signature cycle matrix corresponding to a single cycle of the patient signal data by segmenting the patient signal data into multiple portions. The signature cycle matrix may further be segmented into sub-matrices corresponding to different levels. Properties of the sub-matrices may then be determined to generate diagnostic results.

10 Claims, 8 Drawing Sheets

MATRIX-BASED PATIENT SIGNAL ANALYSIS

TECHNICAL FIELD

The present disclosure generally relates to systems and methods for matrix-based patient signal analysis.

BACKGROUND

The most predominant killers of Americans are Coronary Artery Disease (CAD), heart-related problems and cardiac disorders. Cardiac electrophysiological response and activity analysis are critical for the management of cardiac disorders in the heart tissue and cells, such as ventricular myocardial ischemia caused by a lack of blood oxygen. The clinical reference standard for evaluating cardiac rhythm and events is the 12-lead electrocardiogram (ECG) or multi-channel intra-cardiac electrograms (ICEG).

Currently, analysis of waveform morphologies and time-domain parameters, such as P wave, QRS complex, ST segment, T wave, etc., are used for identifying cardiac arrhythmia events, such as atrial fibrillation (AF), myocardial ischemia (MI), ventricular tachycardia/fibrillation (VT/VF), and so forth. However, the waveform morphologies and time domain parameter analysis are sometimes subjective and time-consuming, and requires extensive medical expertise and clinical experience for accurate interpretation and proper cardiac rhythm management.

Recent research efforts have started to apply more sophisticated mathematical theories to biomedical signal interpretation, such as frequency analysis, symbolic complexity analysis and signal entropy evaluation. However, cardiac electrophysiological (EP) signals (e.g., ECG and ICEG) vary with time and current signal analysis usually cannot localize the precise malfunction severity and trend of cardiac events (e.g. the myocardial ischemia and infarction), such as cardiac pathology irregularity stages, arrhythmia occurrence, drug delivery evaluation, etc.

Known clinical methods typically focus on overall EP signal voltage amplitude analysis for detecting arrhythmia. These methods may not use all the information provided by the EP signals, such as electrophysiological excitation and response activities during the tissue contraction (depolarization) and tissue reperfusion (repolarization). Cardiac abnormality and arrhythmia related information (e.g., timing, energy, etc.), especially in the early stage, may not be efficiently and effectively extracted and characterized by current clinical approaches.

Many traditional medical methods use signal morphology changes to track early cardiac pathologies. However, minute signal morphology changes may not be clearly visible and it is hard to quantitatively evaluate and quantify, for example, QR slope shape change without R peak and Q peak amplitude voltage changes. In addition, there is no known efficient approach to integrate all cardiac electrophysiological activities from different parts of the heart into one single mathematical calculation.

Further, known clinical evaluations may not be efficiently applicable in some cases. For example, myocardial ischemia (MI) detections usually use the golden standard based on ST segment voltage deviation (e.g., 0.1 mV elevation). There are at least two shortcomings with this golden standard for MI analysis: (A) This standard only works for surface ECG signals, but not for intra-cardiac electrogram (ICEG) signals; and (B) the ST segment deviation (voltage) cannot be utilized as a quantitative method for myocardial ischemia severity diagnosis and characterization.

Usually, surface ECG signal analysis based on multi-channel waveform time domain parameters are utilized for cardiac arrhythmia detection, such as heart rate variability (HRV), cardiac wave morphology, R wave, ST segment and T wave amplitudes, etc. However there are no efficient quantitative methods available for cardiac status detection and characterization (e.g., MI) such as quantitative characterization of severity of ongoing ischemia events with chest pain, discomfort, etc. Additionally, most clinical approaches for cardiac arrhythmia identification based on ECG signals are subjective and need extensive clinical expertise and knowledge for accurate pathology interpretation and proper cardiac rhythm management. Furthermore, current known ischemia event detection algorithms may cause false alarms due to single parameter analysis. For example, the amplitude voltage of the ST segment may not be able to provide the severity level of the ischemia event, and heart rate variability may not be able to provide the arrhythmia urgency level either.

SUMMARY

The present disclosure relates to a framework for facilitating patient signal analysis. In accordance with one aspect, the framework generates a signature cycle matrix corresponding to a single cycle of the patient signal data by segmenting the patient signal data into multiple portions. The signature cycle matrix may further be segmented into sub-matrices corresponding to different levels. Properties of the sub-matrices may then be determined to generate diagnostic results.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the system and methods described herein may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

The present framework provides a methodology to analyze patient signals. In accordance with one aspect, the framework analyzes the signature cycle vector (e.g., timing, amplitude, etc.) and matrix pattern generated from an electrophysiological (EP) patient signal. Such analysis may be used to more reliably and precisely characterize cardiac arrhythmia and heart tissue functionality, such as atrial or ventricular functions for detecting early stages of atrial fibrillation, myocardial ischemia-infarction, etc.

Cardiac functional abnormality or arrhythmia usually causes cardiac tissue performance (contracting and reperfusion) to be irregular and may reduce blood flow to regions of the heart, where cells respond by altering action potentials. The changes in these individual cells manifest in local electrograms during depolarization (action potential rising edge) and repolarization (action potential falling edge), reducing signal energy (hyperkalemia or anoxia) or creating multi-phasic waveforms (decoupling). In some implementations, cardiac cycle signal vector and matrix-based pattern-mode analysis is provided to integrate characteristics of different cardiac functional modules (e.g., atrium, ventricle, any electrical potential pathway, etc.).

The framework described herein may generate various matrix properties and indices, such as matrix determinant, matrix trace, matrix-submatrix sequential index, etc., to characterize cardiac electrophysiological activities more accurately with better sensitivity and stability, especially in noisy conditions. The cardiac waveform signature vector and matrix pattern-mode evaluations may include characterization of critical ROI electrophysiological activity (e.g., R wave vector, T wave vector, etc.) within the same heartbeat. Such characterization may be used in real-time monitoring of cardiac tissue pathology (especially ventricular ischemia and infarction), such as in the application of implantable devices. The present framework may advantageously provide a more efficient, accurate and reliable method for identifying cardiac disorders, differentiating cardiac arrhythmias, characterizing pathological severities, predicting life-threatening events, and even evaluating drug delivery effects and providing treatment suggestions or evaluation.

Figure 1:
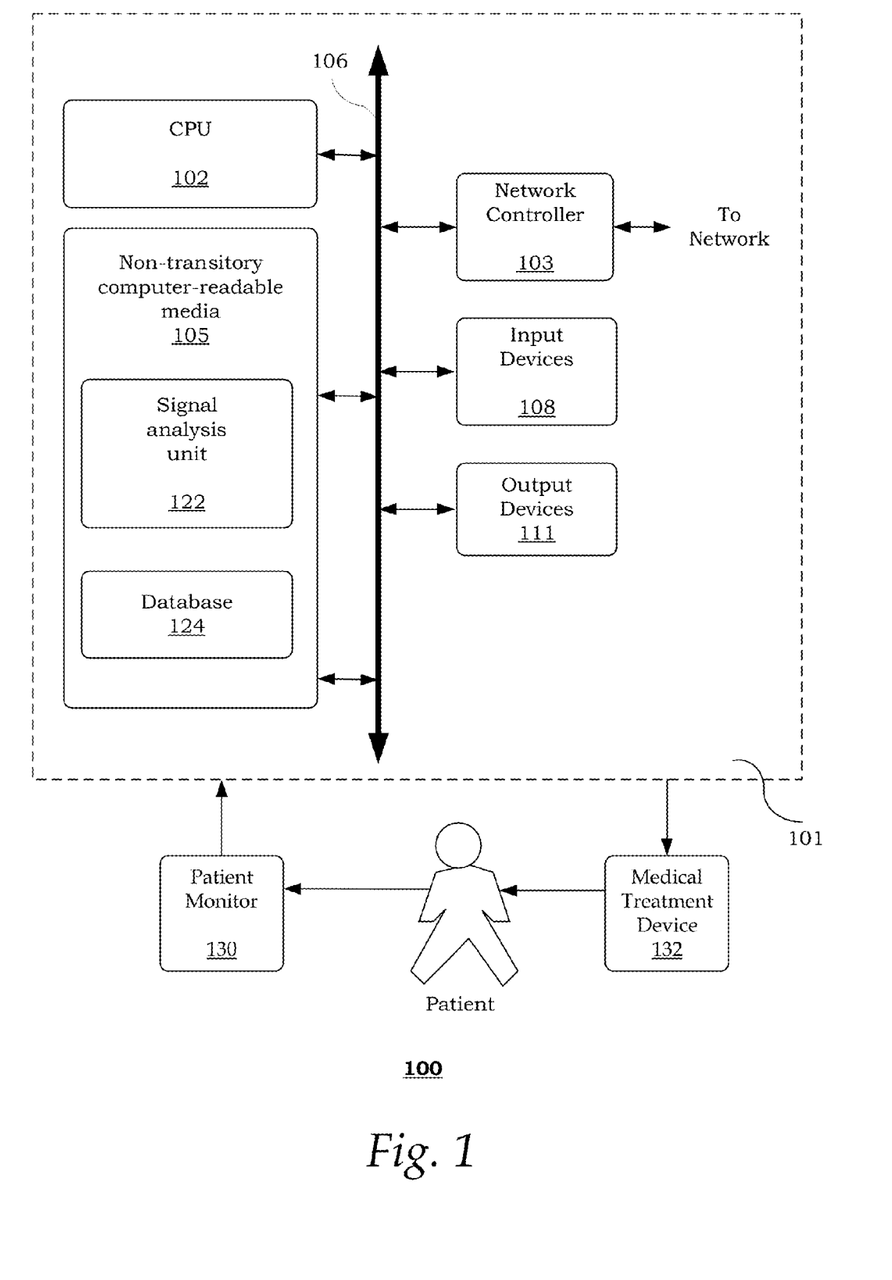
FIG. 1 shows an exemplary system.

FIG. 1 shows an exemplary system 100 for implementing a method and system of the present disclosure. It is to be understood that, because some of the constituent system components and method steps depicted in the accompanying figures can be implemented in software, the actual connections between the systems components (or the process steps) may differ depending upon the manner in which the present framework is programmed. For example, the system 100 may be implemented in a client-server, peer-to-peer (P2P) or master/slave configuration. In such configurations, the system 100 may be communicatively coupled to other systems or components via a network, such as an Intranet, a local area network (LAN), a wide area network (WAN), a P2P network, a global computer network (e.g., Internet), a wireless communications network, or any combination thereof. Given the teachings of the present invention provided herein, one of ordinary skill in the related art will be able to contemplate these and similar implementations or configurations of the present invention.

As shown in FIG. 1, the system 100 may include a computer system 101, a patient monitor 130 and a medical treatment device 132. The computer system 101 may include, inter alia, a central processing unit (CPU) or processor device 102, a non-transitory computer-readable media 105, one or more output devices 111 (e.g., printer, display monitor, projector, speaker, etc.), a network controller 103, an internal bus 106 and one or more input devices 108, for example, a keyboard, mouse, touch screen, gesture and/or voice recognition module, etc. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein may be implemented as computer-readable program code tangibly embodied in non-transitory computer-readable media 105. Non-transitory computer-readable media or memory device 105 may include random access memory (RAM), read only memory (ROM), magnetic floppy disk, flash memory, and other types of memories, or a combination thereof. The present techniques may be implemented by patient signal analysis unit 122 that is stored in computer-readable media 105. As such, the computer system 101 is a general-purpose computer system that becomes a specific-purpose computer system when executing the computer-readable program code.

The same or different computer-readable media 105 may be used for storing a database 124. Database 124 may include a repository of determined parameters and ratios, selectable predetermined functions, patient signal data (e.g., electrophysiological, ECG, ICEG, respiration signal data, other hemodynamic or vital sign data, etc.), patient data (e.g., demographic data, pathology history, etc.), other input data and/or other derived output parameters. Patient signal data may be provided by a patient monitor 130 that is communicatively coupled to the computer system 101.

Patient monitor 130 may be used to acquire various types of patient biometric or electrophysiological signal information for monitoring the patient. For example, the monitoring information may include, but is not limited to, electrophysiological signal data (e.g., ECG, ICEG, etc.), oximetric or SPO2 signal data, respiration signal data, blood pressure, temperature and/or other patient biometric, physiological, hemodynamic, vital sign or medical parameter information. The patient monitor 130 may include appropriate biometric sensors (e.g., leads for surface ECG and basket catheter for intra-cardiac electrographic signal data) for acquiring the monitoring patient signals. Implementations of the present framework provide parameters to detect, diagnose and quantify such patient signals.

Medical treatment device 132 may be automatically and adaptively controlled by the computer system 101 in a closed-loop feedback control system. Medical treatment device 132 may include, but are not limited to, a pacing device, ablator, cardioverter, defibrillator, and so forth. Control parameters of the medical treatment device 132, such as the pacing parameter, ablation energy control, etc., may be automatically determined by computer system 101.

Figure 2:
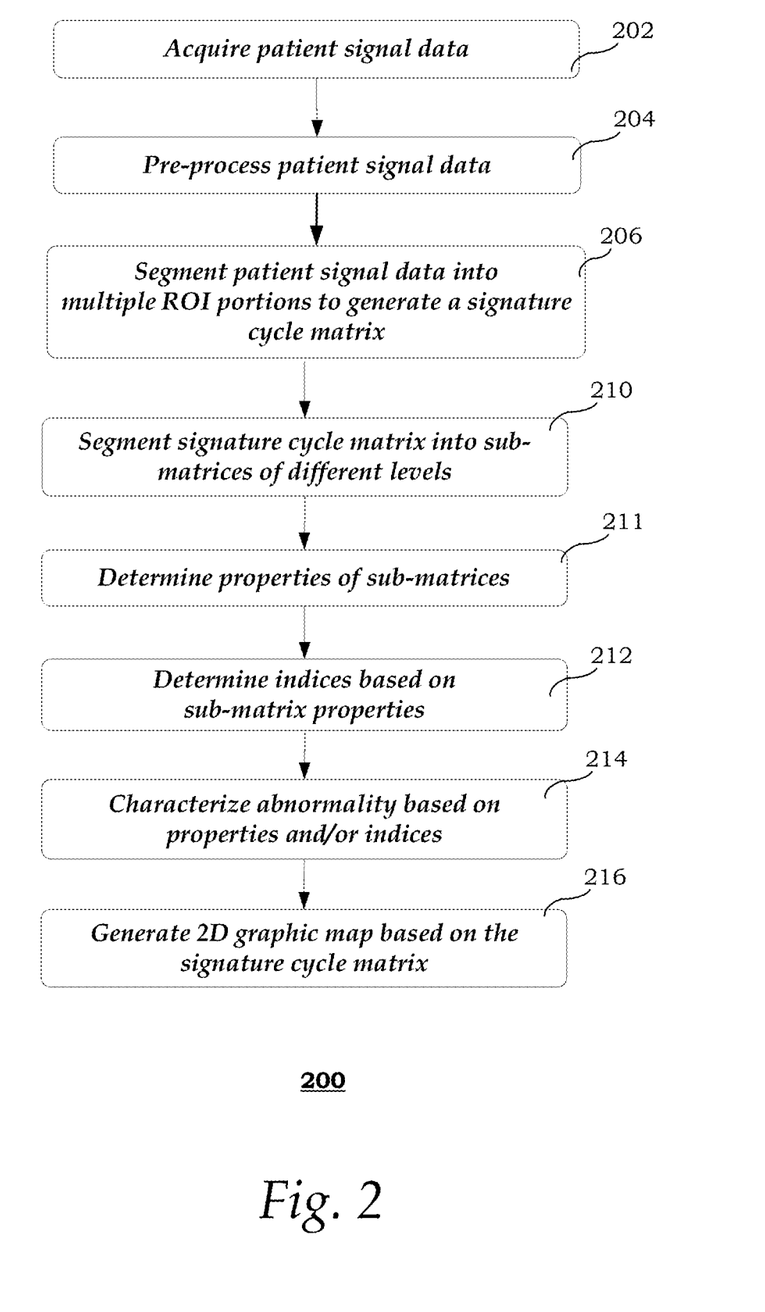
FIG. 2 shows an exemplary method of analyzing patient signals.

FIG. 2 shows an exemplary method 200 of analyzing patient signals. The steps of the method 200 may be performed in the order shown or a different order. Additional, different, or fewer steps may be provided. Further, the method 200 may be implemented with the system 100 of FIG. 1, a different system, or a combination thereof.

At 202, patient monitor 130 acquires patient signal data from a current patient. In some implementations, the patient signal data comprises cardiac electrophysiological signal data, such as intra-cardiac electrographic (ICEG) data, surface ECG data, etc. The cardiac electrophysiological signal data may be acquired by multiple channels connected to, for example, an intra-cardiac basket catheter placed into the heart. Alternatively, or additionally, other types of electrophysiological signal data, such as hemodynamic (HEMO) signal data, respiration (or capnographic) signal data, blood pressure data, oximetric (SPO2) data, and/or other vital sign signal data, other measurable patient biometric, physiological or medical signals, may also be acquired. In addition, other patient information, such as demographic data, clinical application and patient status, including, but not limited to, weight, height, gender, age, allergies, medications, pathology history, pathology treatment history, etc., may also be acquired.

At 204, the patient signal data is pre-processed. The patient signal data may be pre-processed by conditioning, filtering, amplification, digitization and/or buffering. For example, the patient signal data may be pre-filtered and amplified for display as a waveform on, for instance, patient monitor 130. The patient signal data may be filtered to remove unwanted patient movement and respiratory artifacts, as well as power line noise. The filter may be adaptively selected in response to data indicating clinical application (e.g., ischemia detection application, rhythm analysis application). The patient signal data may be conditioned, amplified, buffered, filtered and/or digitized to produce a continuous stream of digitized samples.

In some implementations, a baseline value or signal is automatically extracted from the digitized patient signal data. The baseline value (or signal) generally refers to a known threshold value (or benign signal) with which an unknown value (e.g., amplitude) is compared when measured or assessed. The baseline value may be used in, for example, threshold determination. The baseline value may comprise a zero voltage line if a static (DC) voltage signal component is filtered out from the signal. The baseline value may be adaptively adjusted according to the current application and clinical requirements. Alternatively, if the value is not to be automatically determined, the user may manually select it via, for example, a user interface.

At 206, patient signal analysis unit 122 segments the patient signal data into multiple portions to generate a signature cycle matrix. The signature cycle matrix corresponds to a single signal cycle (e.g., heartbeat). Each row or column of the signature cycle matrix represents signal data values (e.g., amplitude or time duration values) corresponding to a particular portion of the signal cycle. Each portion represents a region of interest (ROI) identified for further analysis. Based on the clinical application, different methods may be used to segment the patient signal waveform (e.g., amplitude, timing, frequency, energy, signal slope speed, etc.) at different levels to capture small signal changes in, for example, morphology, amplitude, timing, latency, energy, etc. A signature cycle matrix may then be constructed based on wave vectors derived from the segmented ROI portions.

Figure 3:
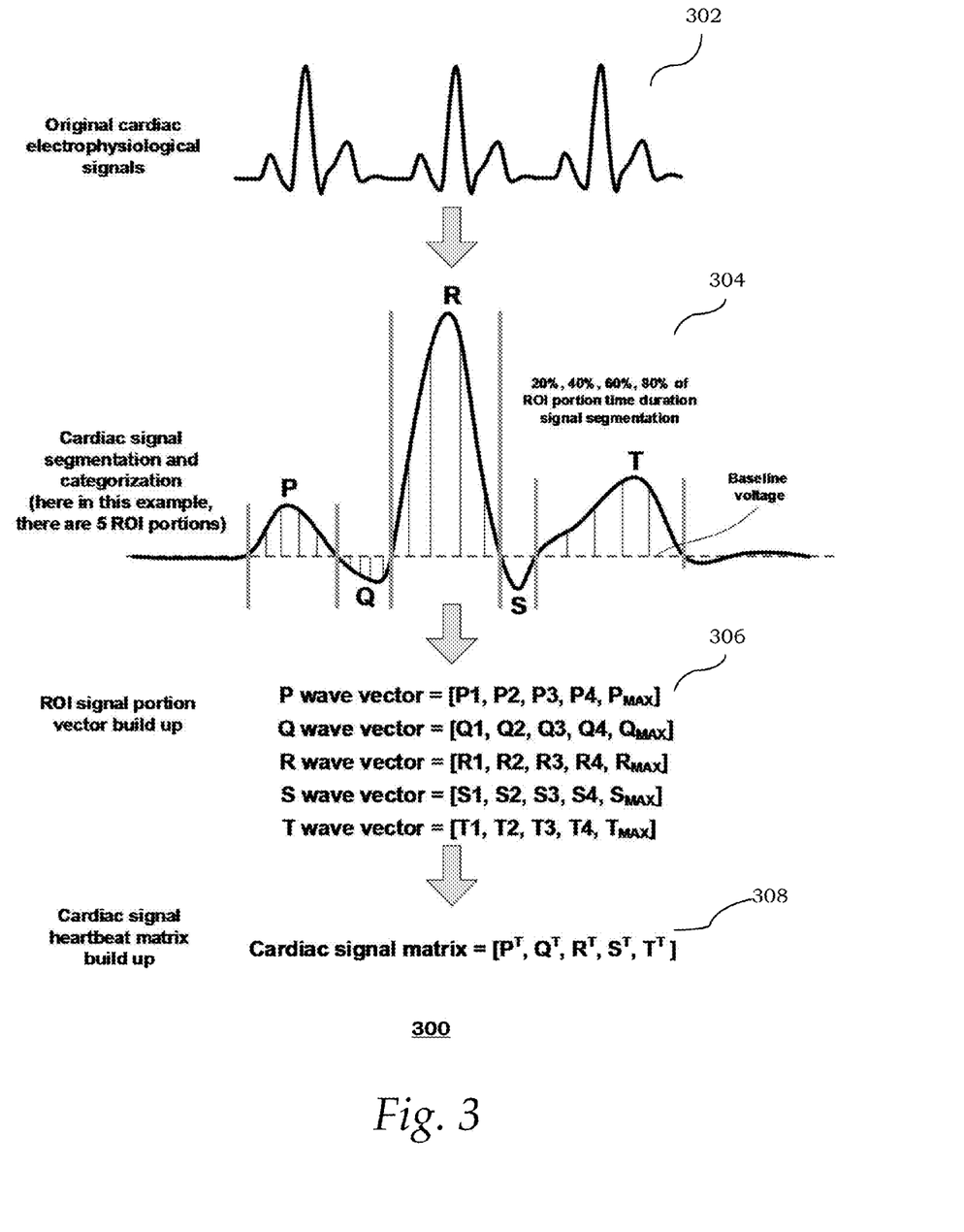
FIG. 3 illustrates an exemplary method of amplitude segmentation.

FIG. 3 illustrates an exemplary method 300 of amplitude segmentation. At 302, the original cardiac electrophysiological signal data is received. At 304, the signal data is segmented into various ROI portions. More particularly, a whole heart beat is vertically segmented into several timing slices based on the cardiac waveform function peak and valley distribution. In this example, 5 ROI portions are selected: P, Q, R, S, and T waveform portions which are segmented by the reference or baseline voltage line (voltage of cardiac rest portion). Each ROI portion is further segmented into four sub-portions. For example, each waveform of the ROI portions is vertically segmented into four levels by using 20%, 40% 60%, and 80% points of the respective timing slice or duration. Hence, by using four-level timing categorization, each ROI signal portion may be segmented to derive 4 corresponding amplitude values. It should be appreciated, however, that any other number of levels or sub-portions may be used.

At 306, these 5 segmented ROI signal portions are all utilized to construct the cardiac signature wave vectors. Each wave vector may include values extracted from the sub-portions of the respective ROI signal portion. In this example, each vector includes five voltage amplitude values corresponding to a particular ROI signal portion. For example, P1, P2, P3 and P4 are the segmented amplitudes in the P wave ROI portion. The wave vector may further include the maximum amplitude value of the associated ROI portion (e.g., $P_{max}$, $Q_{max}$, $R_{max}$, $S_{max}$ or $T_{max}$). The number of amplitude value points (e.g., 5) may be selected to match the total number of the ROI portions (here in this example, there are 5 ROI portions) so as to create a square matrix at step 308. Based on the clinical application and user preference, clinical users or computer software algorithms may adaptively select the number and locations of the ROI signal portions, modify the size of the segmentation point series, and/or update the size of the signal vector and matrix. At 308, a 5×5 cardiac signature cycle matrix is constructed based on the transpose of the wave vectors (e.g., $P^T$, $Q^T$, $R^T$, $S^T$ and $T^T$), which may be used for further calculation and diagnosis.

Figure 4:
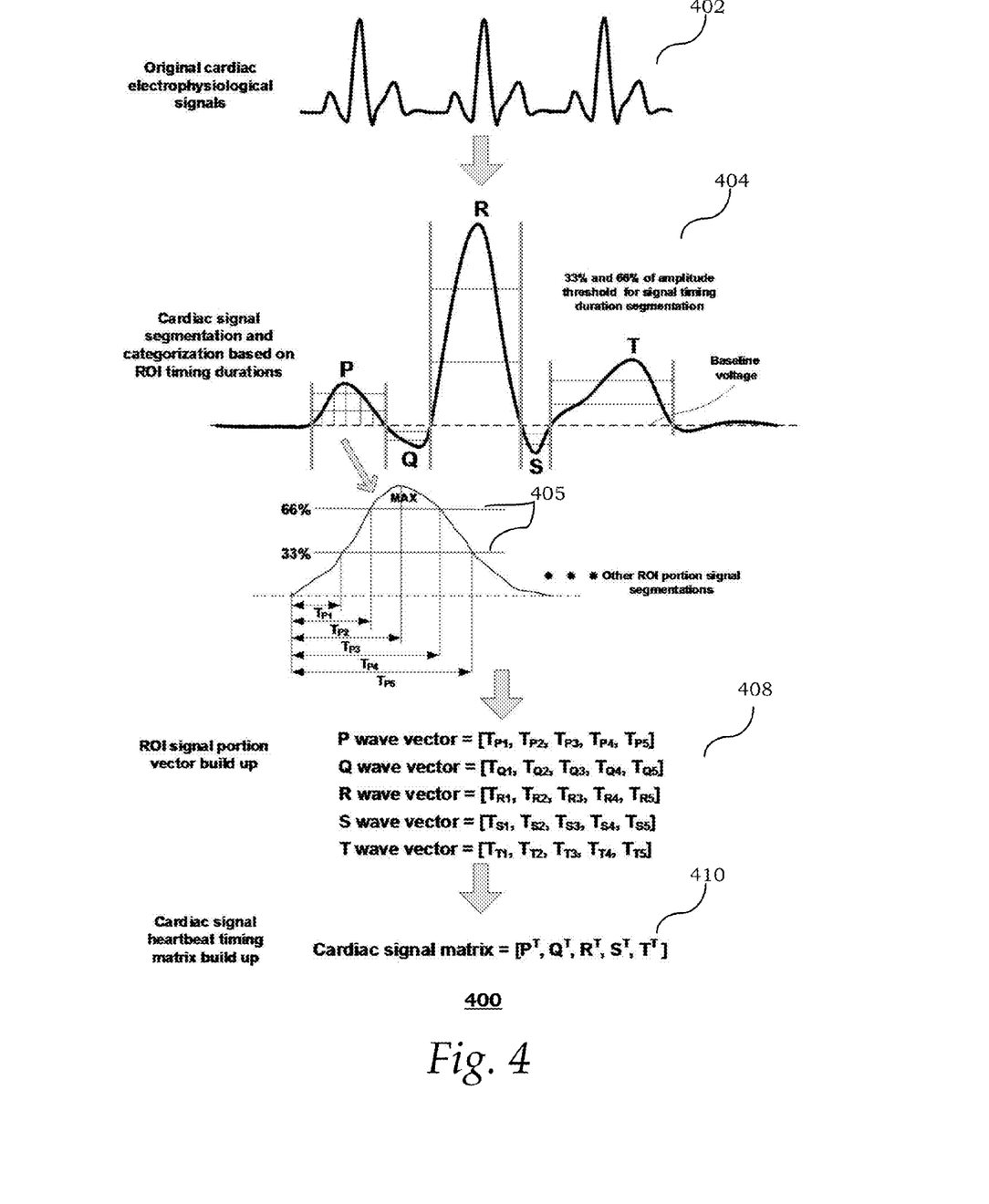
FIG. 4 illustrates an exemplary method of timing duration segmentation.

FIG. 4 illustrates an exemplary method 400 of timing duration segmentation. At 402, the original cardiac electrophysiological signal data is received. At 404, the signal data is segmented into various ROI portions. In this exemplary timing duration segmentation, two voltage thresholds (405)—33% and 66% of the maximum voltage amplitude of the corresponding ROI portion—are used to separate the time duration of the corresponding ROI portion and derive five time points ($T_{P1}$ to $T_{P5}$) that correspond to the voltage thresholds. At 408, the time points ($T_{P1}$ to $T_{P5}$) are used to generate wave vectors (e.g., P wave vector, Q wave vector, R wave vector, S wave vector and T wave vector) for the different ROI portions. For example, a P wave vector may include the time points $T_{P1}$, $T_{P2}$, $T_{P3}$, $T_{P4}$ and $T_{P5}$. At 410, a 5×5 cardiac signature cycle matrix is constructed based on the transpose of the wave vectors (e.g., $P^T$, $Q^T$, $R^T$, $S^T$ and $T^T$), which may be used for further calculation and diagnosis.

Returning to FIG. 2, at 210, patient signal analysis unit 122 segments the signature cycle matrix into sub-matrices of different levels. In some implementations, a sequential sub-matrix extraction method is used to segment the signature cycle matrix into different level sub-matrices. Compared to the full signature cycle matrix, the sub-matrices characterize different features. The full matrix characterizes the entire waveform of the ROI signal portions, including the energy level and similarity, while the sub-matrices characterize similar waveform portions associated with different ROI signal portions.

Figure 5:
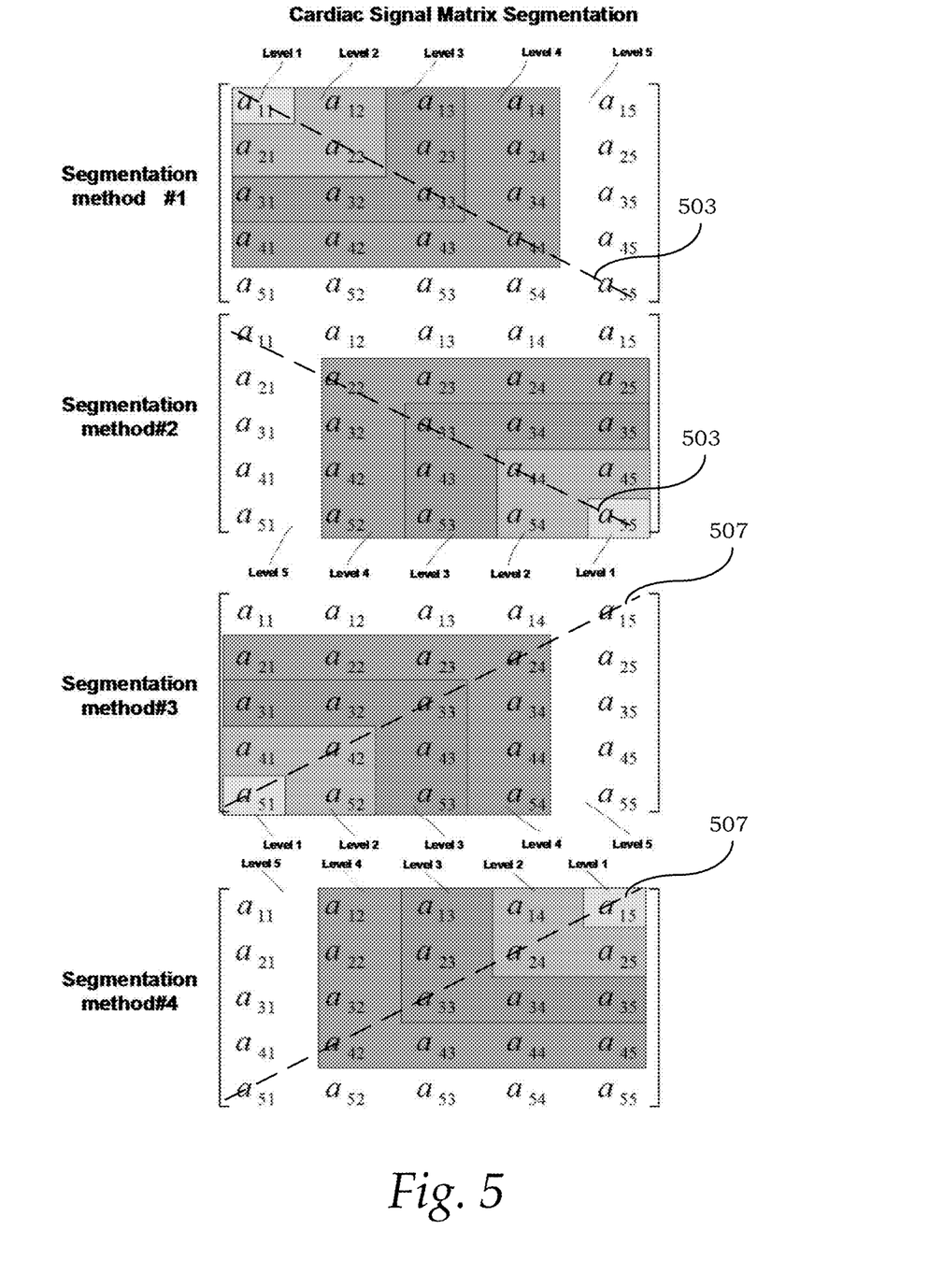
FIG. 5 illustrates four exemplary methods of extracting sub-matrices.

FIG. 5 illustrates four exemplary methods of extracting sub-matrices. The sub-matrices are extracted from a square (N by N) signature cycle matrix (or mother matrix) along the diagonal or inverse diagonal of the mother matrix. In some implementations, five ROI signal portions and corresponding five parameters (e.g., amplitudes or timing durations) are categorized for each ROI area. In the example shown in FIG. 5, the mother matrix is 5 by 5 and there are five levels of segmentation, including the mother matrix itself at level 5.

As illustrated by FIG. 5, sub-matrix segmentation involves categorizing the mother matrix downwards or upwards along the normal diagonal 503 (upper left to lower right), or upwards or downwards along the inverse diagonal 507 (lower left to upper right) of the mother matrix. In addition, the four different matrix segmentation methods also have clinical signal value and meaning. For example, segmentation method #1 shows a linear segmentation of the mother matrix downwards along the normal diagonal 503 of the mother matrix. The segmentation separates the mother matrix into five levels (from left to right) of sub-matrices. It should be appreciated, however, that other number of levels may also be defined.

Level 1 sub-matrix includes a single element (e.g., $a_{11}$) that represents the P wave existence. If the element's value is near zero, it means that P wave may be disappearing. The smaller the element's value is, the higher the severity of the P wave issue. Level 2 sub-matrix is two by two matrix that represents both rising edges of the P wave and Q wave, which can be utilized for rising edge correspondence of the rising speed for P and Q waves. Level 3 sub-matrix is a 3 by 3 matrix that represents the rising edges of the P, Q and R wave ROI portions, which can be utilized for determining rising edge mutual relations (e.g., rising speed and shape) for the P wave, Q wave and R wave ROI portions. Level 4 sub-matrix is a 4 by 4 matrix that includes a maximum value and information of 4 ROI portions (P, Q, R, S waves), which can be utilized for determining signal similarity relations of the signal shapes for the P wave, Q wave, R wave and S wave. Finally, level 5 sub-matrix is the 5 by 5 mother matrix of all ROI portions that includes information from all 5 ROI portions (P, Q, R, S and T waves), which can be utilized for determining signal shape and energy relations of all the ROI signal waveform portions. Accordingly, by using such matrix segmentation, different levels of sub-matrices can be generated, which may be used for further calculation and pattern-mode diagnosis and characterization, such as determining pathology severity, arrhythmia location, disease type, etc.

Returning to FIG. 2, at 211, patient signal analysis unit 122 determines properties of the sub-matrices. Such properties serve to show or detect any change in the entries (or elements) of the sub-matrices. In some implementations, two specific properties are utilized for cardiac cycle signal diagnosis: trace and determinant. Other properties, such as matrix rank, vector norm, matrix norm, etc., may also be used. The properties may also be combined to differentiate cardiac cycle signal changes in some clinical applications.

The trace (TR) of an N-by-N square sub-matrix A may be defined as a sum of the elements on the main diagonal (e.g., diagonal from the upper left to the lower right) of A, as follows:

$$\text{TRACE(cardiac signal matrix)} = TR(A) = \sum_{i=1 \text{ to } N} a_{ii} \quad (1)$$

$$|\text{TRACE(cardiac signal matrix)}| = |TR(A)| = \sum_{i=1 \text{ to } N} |a_{ii}| \quad (2)$$

wherein $a_{ii}$ denotes the entry on the i-th row and i-th column of sub-matrix A.

The determinant (Det) of an N-by-N square sub-matrix A may be determined from entries of the matrix by a specific arithmetic expression (e.g., Leibniz formula or Laplace formula), such as follows:

$$\text{Det}(A) = \sum_{\sigma \in S_N} \text{SGN}(\sigma) \prod_{i=1}^{N} a_{i,\sigma_i} \quad (3)$$

wherein Det(A) is computed over all permutations σ of the set $S_N = \{1, 2, \ldots, N\}$. A permutation is a function that reorders this set of integers. The value in the $i^{th}$ position after the reordering function a is denoted as $\sigma_i$. The set of all such permutations is denoted as $S_N$ for each permutation σ; SGN(σ) denotes the signature of σ, a value that is +1 whenever the reordering given by a can be achieved by successively interchanging two entries an even number of times, and −1 whenever it can be achieved by an odd number of such interchanges.

At 212, patient signal analysis unit 122 determines indices based on the properties of the sub-matrices. In order to more efficiently diagnose and characterize the ROI signal portion changes, a sequential energy index ($SMEI_{Trace}$) may be derived based on a sum of squared magnitudes of trace values corresponding to the sub-matrices as follows:

$$SMEI_{Trace} = \sum_{i \in Level\_number} |TRACE_i|^2 \quad (4)$$

wherein Level_number is the total number of levels in the matrix segmentation, including the last level of segmentation that results in the mother matrix; $TRACE_i$ is the trace value of the level i sub-matrix.

A sequential energy index ($SMEI_{Determinant}$) may also be derived based on a sum of squared magnitudes of the determinant values corresponding to the sub-matrices as follows:

$$SMEI_{Determinant} = \sum_{i \in Level\_number} |Det(A_i)|^2 \qquad (5)$$

wherein Level_number is the total number of levels in the matrix segmentation, including the last level of segmentation that results in the mother matrix; $Det(A_i)$ is the determinant value of the level i sub-matrix.

At 214, patient signal analysis unit 122 characterizes an abnormality based on the sub-matrix parameters and/or indices. The abnormality may include, for example, cardiac arrhythmia or myocardial ischemia. In some implementations, the location, severity, type and/or timing of cardiac pathologies are determined based on the sub-matrix parameters (e.g., determinant, trace, etc.) and/or indices (e.g., sequential energy index) derived therefrom. The working pattern and dynamic mode of the whole cardiac cycle may be derived for synchronizing multiple ROI signal portions and integrating data derived from different parts of the same cardiac cycle.

Figure 6:
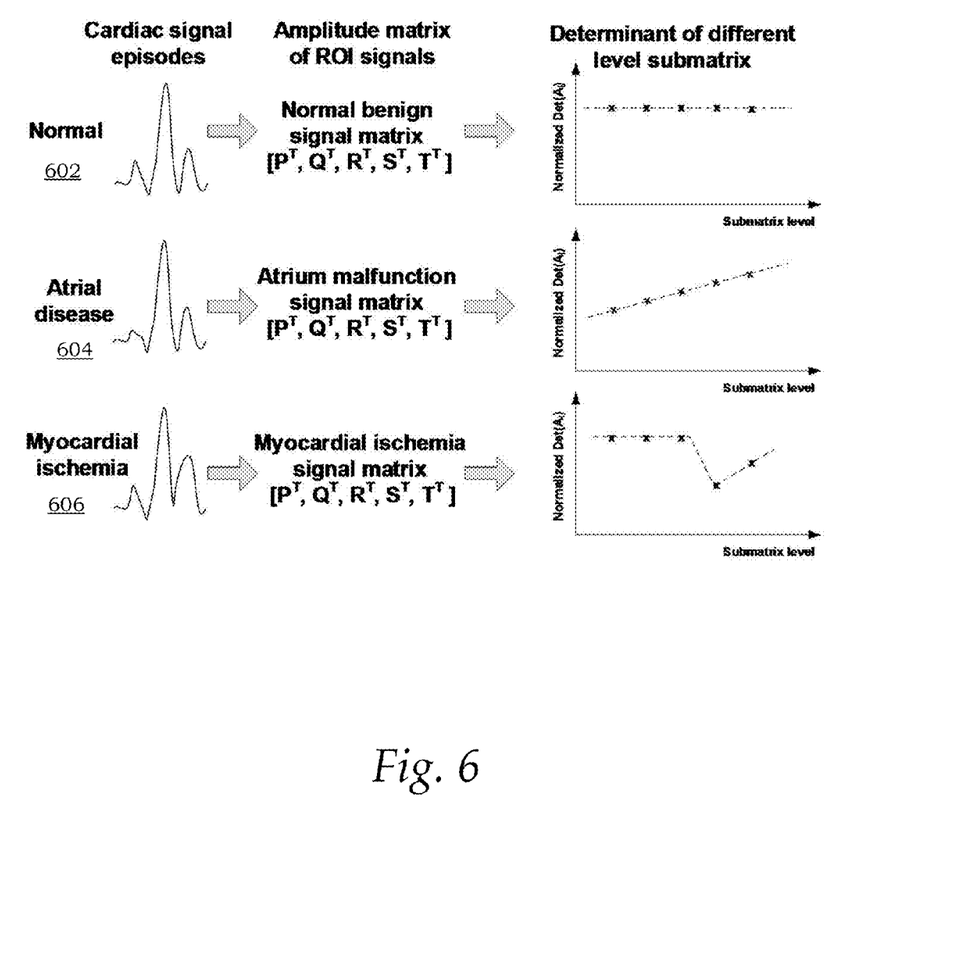
FIG. 6 shows a computer simulation of three exemplary cardiac episodes for comparison.

FIG. 6 shows a computer simulation of three exemplary cardiac episodes for comparison: normal (602), atrial disease (604) and myocardial ischemia (606). The normal episode refers to a benign cardiac cycle and the determinant values for amplitude sub-matrices of different levels are used as reference for normalizing the determinant values associated with the sub-matrices of corresponding levels. For example, the user or framework may divide a given determinant parameter value with the determinant parameter value of the benign reference sub-matrix at the same level.

If there is an atrial disease (604) that causes the signal amplitude to be smaller, all level determinant values become smaller. The sequential determinants of different levels shows a sloping trend. The slope degree and direction may also be used as quantitative parameters for detecting and characterizing cardiac arrhythmia. If there is myocardial ischemia event (606), which occurs at the T wave portion, the low level (e.g., 1-3) sub-matrix determinant values do not show any changes while the high level (e.g., 4-5) sub-matrix determinant values show drastic changes, especially in level 4 (>40% change). By using this simulation example, it can be shown that sub-matrix parameters can be used to monitor and characterize the location, type, severity and timing of cardiac signal changes.

For purposes of illustration, FIG. 6 shows three individual cardiac cycle diagnoses based on determinants derived from multi-level sub-matrices. It should be appreciated, however, that other sub-matrix properties and/or indices, such as trace, determinant and energy index, may also be used for diagnosis. In addition, this sub-matrix pattern diagnosis approach may be developed for continuous and real-time application, such as for real-time patient monitoring and health alarm system. The trace, determinant and energy index values derived from the different level sub-matrices may be re-organized for dynamic statistical analysis. For example, parameters and/or or indices derived from level 2 sub-matrices of a sequential cardiac cycles may be constructed into time series data. By extracting and reconstructing the dataset, parameters and indices, different kinds of methods, such as variation and variability, matrix entropy, hypothesis tests for qualitative and quantitative diagnosis, may be implemented.

Patient electrophysiological signal vector and matrix analysis may provide different kinds of information to the clinical users, such as amplitude change, timing changes, cardiac pathology severity, cardiac arrhythmia potential location, and/or treatment suggestions and methods. In order to more efficiently combine all patient data and associated parameters and/or indices, an artificial neural network (ANN) may be used. The ANN may non-linearly fuse all available data to provide a set of diagnostic results for use by a doctor to make informed decisions. Other types of methods, such as a fuzzy system or expert system, may also be used for data fusion. Statistical and hypothesis testing algorithms may also be fulfilled with ANN nonlinear data fusion and diagnosis.

Figure 7:
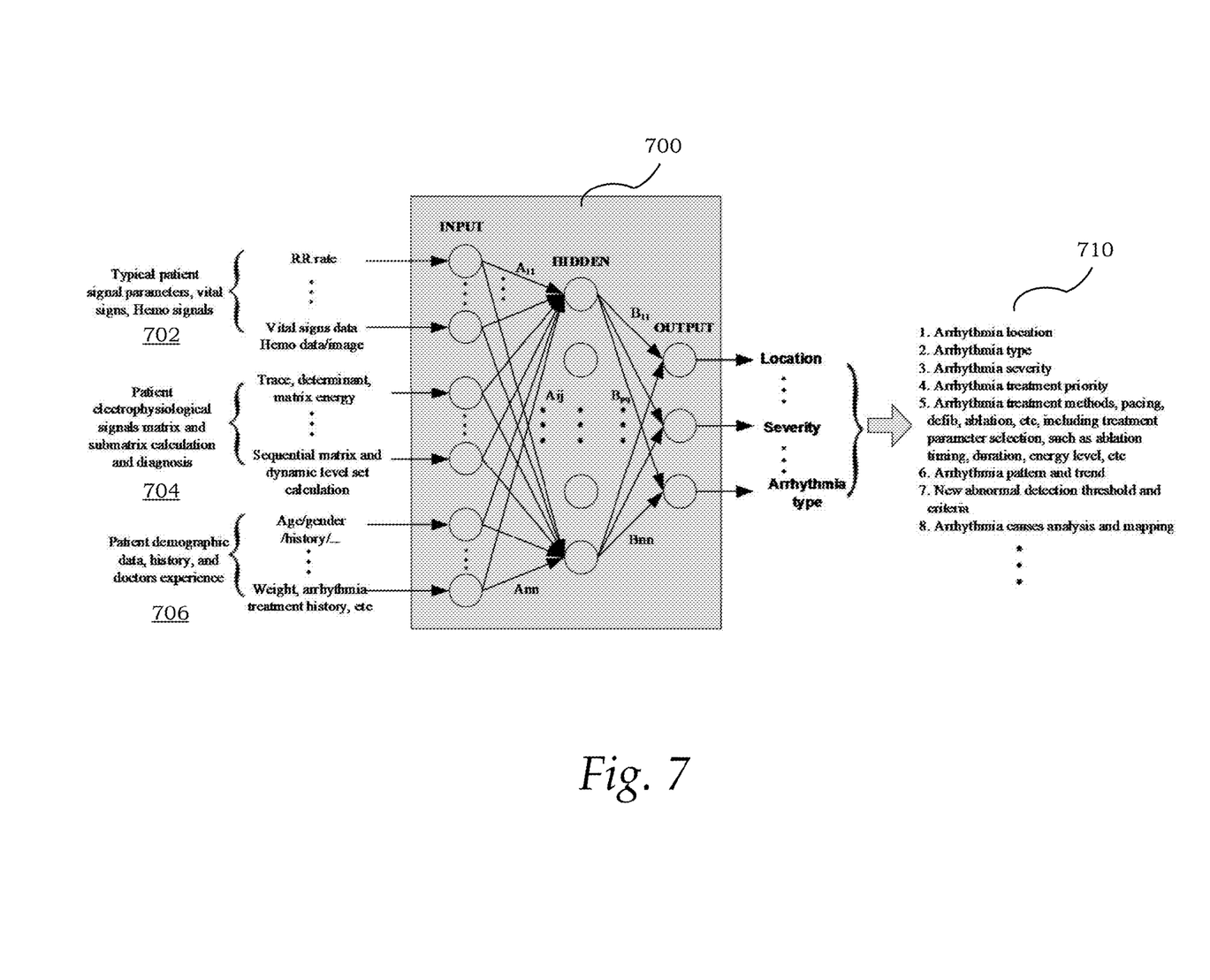
FIG. 7 shows an exemplary artificial neural network (ANN) module.

FIG. 7 shows an exemplary ANN module 700. The ANN module 700 includes 3 layers: (1) input layer, (2) hidden layer and (3) output layer. Weights ($A_{11}$ to $A_{nn}$ and $B_{11}$ to $B_{nn}$) between the layers may be adaptively adjusted with a training data set. The ANN module 700 has a self-learning ability with new input data, which can increase the accuracy of the calculated results 710. The ANN module 700 combines patient signal data 702 (e.g., vital sign, hemodynamic signal data, etc.), different sub-matrix parameters and indices 704 generated by the present framework (e.g., trace, determinant, energy, sequential matrix index, dynamic level set, etc.), patient data (e.g., demographic data, treatment history, etc.) and information derived from the doctor's experience 706 to generate quantitative and qualitative output results 710. The output results 710 include detailed patient status and treatment parameters for optimized cardiac rhythm management (CRM), such as cardiac arrhythmia type, severity, location mapping, trend, etc., as well as suggestions for treatment, such as treatment location, priority, treatment control parameter (e.g., pacing parameter, ablation energy control, etc.), and so forth.

At 216, patient signal analysis unit 122 generates a two-dimensional (2D) graphic map based on the signature cycle matrix. The signature cycle matrix clinically corresponds to a cardiac response signal cycle and can be graphically mapped to patient heart activities for visualization. Severity or deviation degrees of signal may also be color coded in the graphic map.

Figure 8:
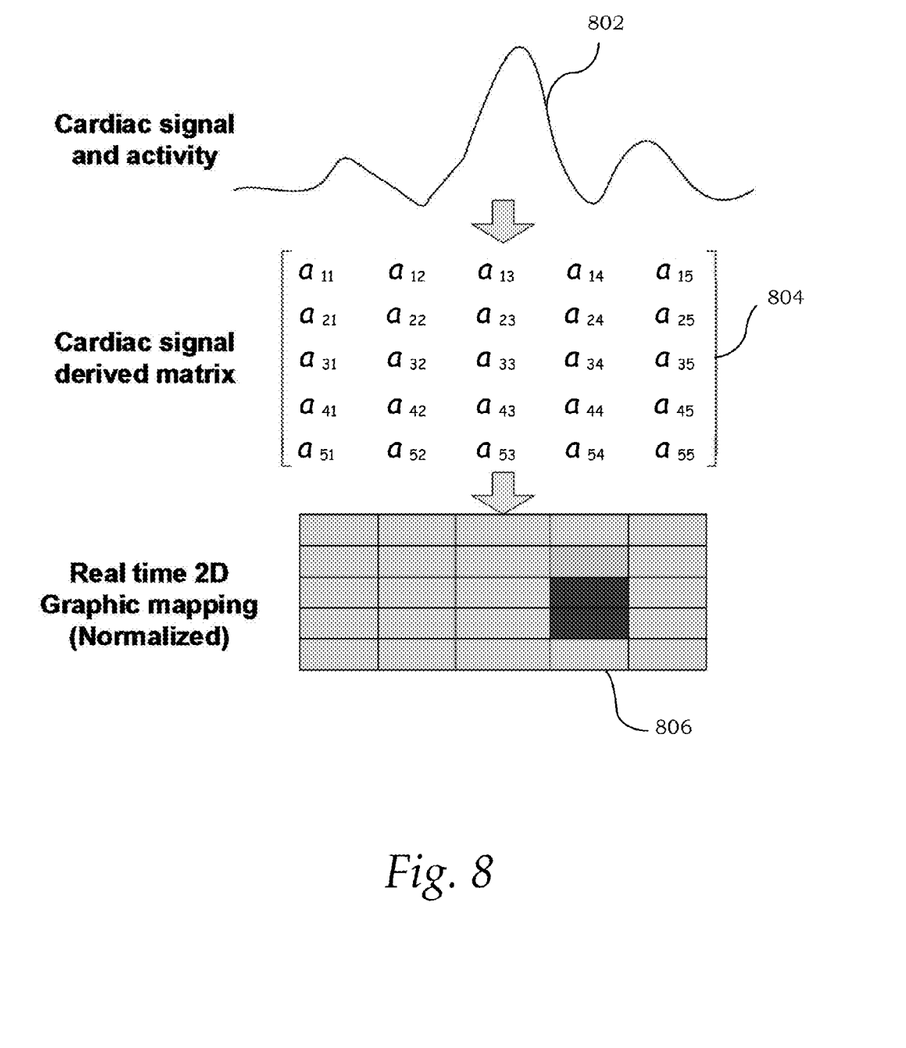
FIG. 8 illustrates the mapping of a cardiac signal to a two-dimensional (2D) graphic map.

FIG. 8 illustrates the mapping of a cardiac signal 802 to a 2D graphic map 806 via its derived signature cycle matrix 804. Each entry in the derived signature cycle matrix 804 may be mapped to an element on the 2D graphic map 806. Accordingly, all ROI signal portions (P wave, Q wave, R wave, etc.) are mapped and filled into the graph 806. The color coding of the elements in the 2D graphic map 806 represents the severity or percentage change in the corresponding entry (e.g., amplitude or timing duration). This 2D graphic map may be rendered and presented on a display device in real-time for easy signal monitoring by a user. The 2D changes in color is advantageously more convenient and easier to detect than minute changes in the signal waveform or parameters in the one-dimensional domain.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A system for patient signal analysis, comprising:
 a patient monitor configured to acquire a patient signal data from a patient; and
 a computer system communicatively coupled to the patient monitor, wherein the computer system includes
 a non-transitory memory device,
 a processor device in communication with the memory device, and
 a signal analysis unit stored in the memory device and operative with the processor device to perform steps including
  generating a signature cycle matrix corresponding to a single cycle of the patient signal data by segmenting the patient signal data into multiple portions,
  segmenting the signature cycle matrix into sub-matrices corresponding to different levels,
  determining properties of the sub-matrices,
  determining a sequential energy index based on the properties of the sub-matrices, wherein the sequential energy index comprises a sum of squared magnitudes corresponding to the sub-matrices, and
  characterizing an abnormality based on the properties and the sequential energy index.

2. The system of claim 1 wherein the signal analysis unit is further operative with the processor device to generate the signature cycle matrix by
 segmenting each of the multiple portions into sub-portions,
 generating wave vectors based on values extracted from the sub-portions, and
 generating the signature cycle matrix based on the wave vectors.

3. The system of claim 2 wherein the values comprise voltage amplitude values.

4. The system of claim 3 wherein the voltage amplitude values comprise a maximum voltage amplitude value of a corresponding portion.

5. The system of claim 2 wherein the values comprise time durations.

6. The system of claim 1 wherein the sub-matrices comprise:
 a first level sub-matrix that represents existence of a P wave in the cycle;
 a second level sub-matrix that represents both rising edges of the P wave and a Q wave in the cycle;
 a third level sub-matrix that represents rising edges of the P wave, the Q wave and an R wave in the cycle;
 a fourth level sub-matrix that represents information from the P wave, the Q wave, the R wave and an S wave in the cycle; and
 a fifth level sub-matrix that represents information from the P wave, the Q wave, the R wave, the S wave and a T wave in the cycle.

7. The system of claim 1 wherein the properties comprise trace or determinant values.

8. The system of claim 7 wherein the squared magnitudes comprise magnitudes of trace values corresponding to the sub-matrices.

9. The system of claim 7 wherein the squared magnitudes comprise magnitudes of determinant values corresponding to the sub-matrices.

10. The system of claim 1 wherein the abnormality comprises cardiac arrhythmia or myocardial ischemia.

* * * * *